(12) United States Patent
Taki et al.

(10) Patent No.: US 11,702,094 B2
(45) Date of Patent: Jul. 18, 2023

(54) DRIVING SUPPORT APPARATUS AND DRIVING SUPPORT METHOD

(71) Applicant: TOYOTA JIDOSHA KABUSHIKI KAISHA, Toyota (JP)

(72) Inventors: Toshiki Taki, Toyota (JP); Yohei Hareyama, Ninomiya-machi (JP); Hiroyuki Amano, Susono (JP); Kazuyuki Kagawa, Nagoya (JP); Yuki Takahashi, Susono (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 31 days.

(21) Appl. No.: 17/570,570

(22) Filed: Jan. 7, 2022

(65) Prior Publication Data

US 2022/0258757 A1 Aug. 18, 2022

(30) Foreign Application Priority Data

Feb. 17, 2021 (JP) .................................. 2021-023466

(51) Int. Cl.
*H04N 5/44* (2011.01)
*B60W 50/14* (2020.01)
*B60W 30/095* (2012.01)
*B60W 40/04* (2006.01)
*A61B 5/16* (2006.01)
(Continued)

(52) U.S. Cl.
CPC ............. *B60W 50/14* (2013.01); *A61B 5/162* (2013.01); *A61B 5/18* (2013.01); *B60W 30/0956* (2013.01); *B60W 40/04* (2013.01); *G06N 3/02* (2013.01); *G06V 20/58* (2022.01);
(Continued)

(58) Field of Classification Search
CPC .. B60W 50/14; B60W 30/0956; B60W 40/04; B60W 2050/143; B60W 2050/146; B60W 2554/80; B60W 2556/10; A61B 5/162; A61B 5/18; A61B 5/0077; A61B 5/1176; A61B 2503/22; G06N 3/02;
(Continued)

(56) References Cited

U.S. PATENT DOCUMENTS 5,865,265 A    2/1999   Matsumoto
9,324,233 B2 *  4/2016   Grabow ............... G08G 1/0112
(Continued)

FOREIGN PATENT DOCUMENTS

JP     H07-277041 A    10/1995
JP     2010-117751 A    5/2010
(Continued)

*Primary Examiner* — Munear T Akki
(74) *Attorney, Agent, or Firm* — Oliff PLC

(57) ABSTRACT

The driving support apparatus includes a memory configured to store information representing a degree of familiarity with an environment for a driver of a vehicle; and a processor configured to detect an object existing around the vehicle based on a sensor signal representing a situation around the vehicle obtained by a sensor mounted on the vehicle, determine whether or not the object approaches the vehicle so that the object may collide with the vehicle, and notify the driver of the approach via a notification device mounted on the vehicle at a timing corresponding to the degree of familiarity with the environment for the driver of the vehicle, when it is determined that the object approaches the vehicle so that the object may collide with the vehicle.

6 Claims, 7 Drawing Sheets

(51) Int. Cl.
*A61B 5/18* (2006.01)
*G06V 20/58* (2022.01)
*G06N 3/02* (2006.01)

(52) U.S. Cl.
CPC . *B60W 2050/143* (2013.01); *B60W 2050/146* (2013.01); *B60W 2554/80* (2020.02); *B60W 2556/10* (2020.02)

(58) Field of Classification Search
CPC ...... G06V 20/58; G06V 20/59; G06V 40/171; G06V 40/172
See application file for complete search history.

(56) References Cited

U.S. PATENT DOCUMENTS

| | | | |
|---|---|---|---|
| 10,475,348 B2* | 11/2019 | Kruger | G08G 1/166 |
| 11,104,348 B2* | 8/2021 | Chen | B60W 40/08 |
| 2018/0105184 A1* | 4/2018 | Urano | B60W 30/09 |
| 2018/0215395 A1* | 8/2018 | Keany | G06V 40/19 |
| 2019/0193751 A1* | 6/2019 | Fernando | G08G 1/096883 |
| 2019/0325238 A1* | 10/2019 | Prakah-Asante | B60W 50/14 |

FOREIGN PATENT DOCUMENTS

| | | |
|---|---|---|
| JP | 2013-222297 A | 10/2013 |
| JP | 2015-219531 A | 12/2015 |

* cited by examiner

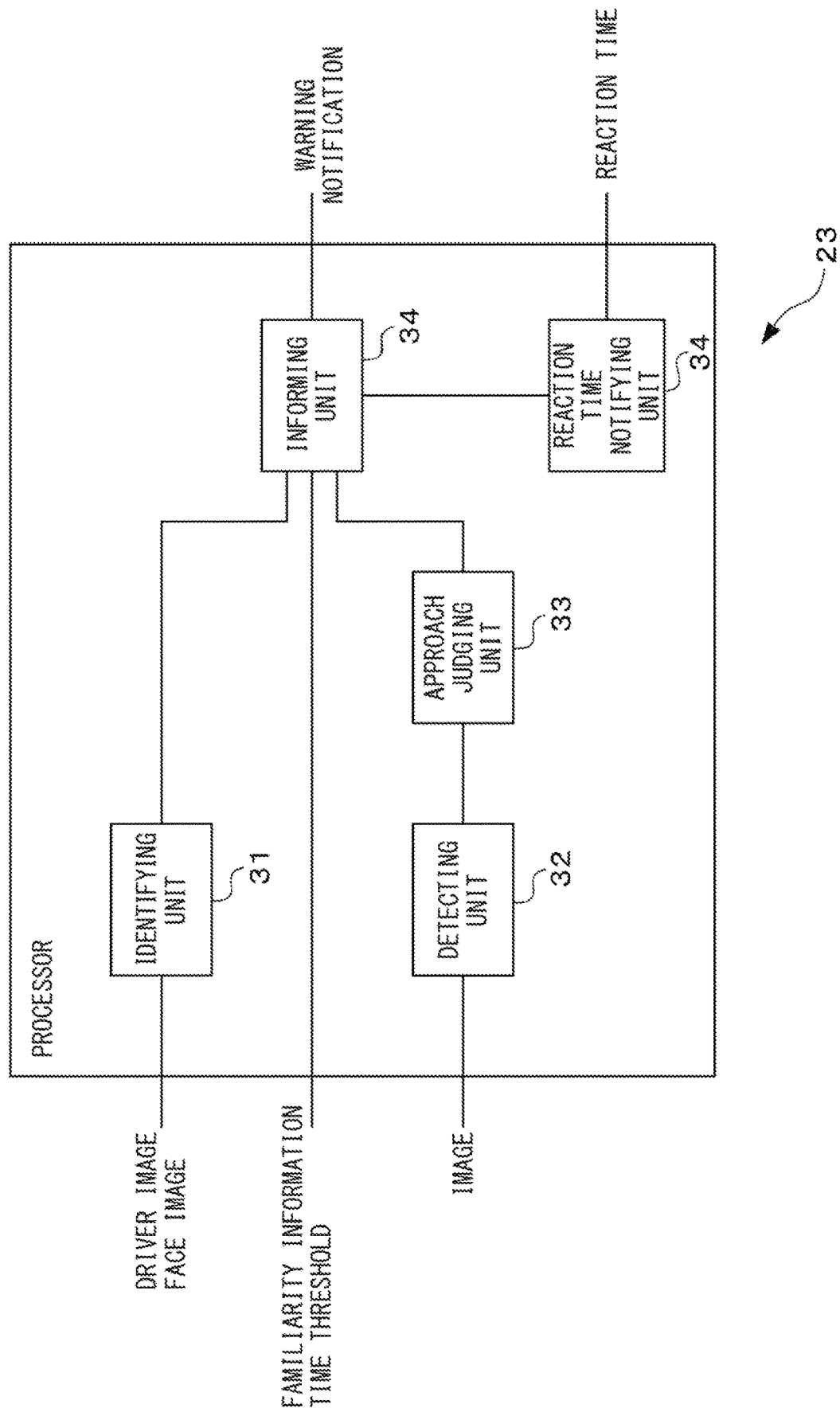

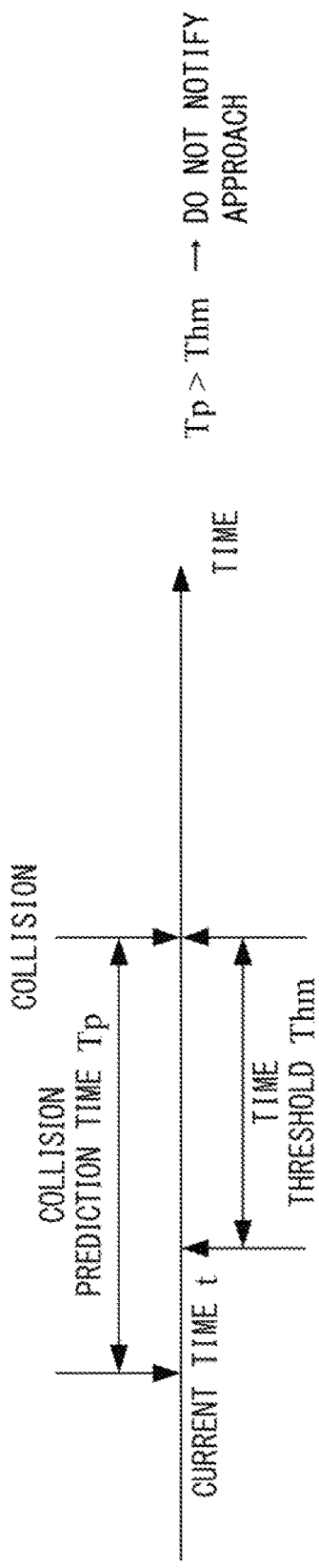
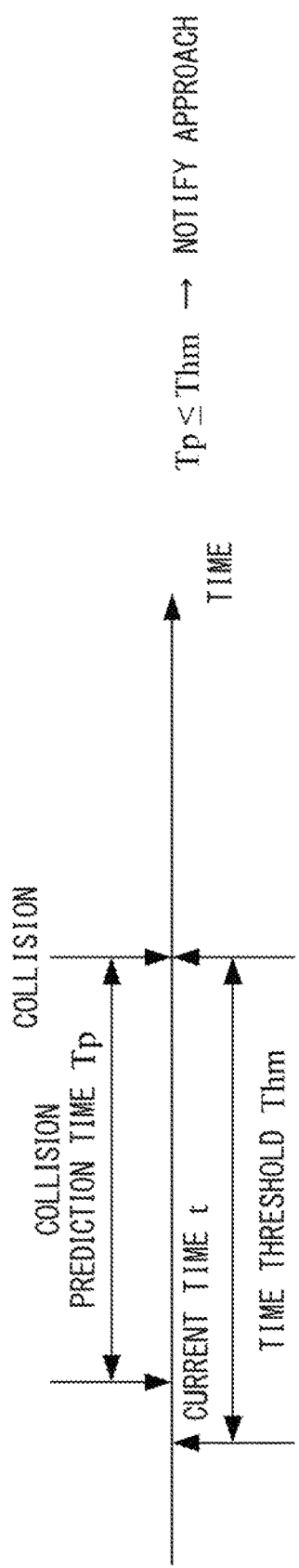

DRIVING SUPPORT APPARATUS AND DRIVING SUPPORT METHOD

CROSS-REFERENCE TO RELATED APPLICATION

This application is based upon and claims the benefit of priority of the prior Japanese Patent Application No. 2021-023466, filed on Feb. 17, 2021, and the entire contents of which are incorporated herein by reference.

FIELD

The present invention relates to a driving support apparatus, a driving support method and a computer program for driving support that alerts, when some danger is detected in the running of the vehicle, the driver to the danger.

BACKGROUND

There has been proposed a technique for calling, when any danger is detected in the running of the vehicle, the driver's attention to the danger (for example, see Japanese Patent Laid-Open No. 2015-219531).

In the technique disclosed in Japanese Patent Application Laid-Open No. 2015-219531, it is determined whether or not the vehicle is in an approaching state based on a detection result by an ambient sensor that detects a distance between an object existing around the vehicle and the vehicle. The approach state is a state in which the vehicle and the object approach less than a predetermined distance, or the vehicle and the object are in contact with each other. When it is determined that the vehicle is in the approaching state, this fact is notified to the driver of the vehicle.

SUMMARY

If the timing of the notification about the approach of the object to the vehicle is too early, the driver may feel troublesome. Conversely, if the timing of the notification about the approach of the object to the vehicle is too slow, the driver may be in a hurry and the driver may not be able to properly perform the operation of the vehicle to avoid the collision with its approaching object.

It is therefore an object of the present invention to provide a driving support apparatus capable of notifying a driver of a vehicle of an approach of an object to the vehicle at an appropriate timing.

According to one embodiment, a driving support apparatus is provided. The driving support apparatus includes: a memory configured to store information representing a degree of familiarity with an environment for a driver of a vehicle; and a processor configured to detect an object existing around the vehicle based on a sensor signal representing a situation around the vehicle obtained by a sensor mounted on the vehicle, determine whether or not the object approaches the vehicle so that the object may collide with the vehicle, and notify the driver of the approach via a notification device mounted on the vehicle at a timing corresponding to the degree of familiarity with the environment for the driver of the vehicle, when it is determined that the object approaches the vehicle so that the object may collide with the vehicle.

In the driving support apparatus, it is preferable that, when it is determined that the object approaches the vehicle so that the object may collide with the vehicle, the processor calculates a predicted time until the collision, and when the predicted time is less than or equal to a time threshold representing the timing set to be shorter as the degree of familiarity with the environment of the driver is higher, the processor notifies the driver of the approach.

In this case, it is preferable that the information representing the degree of familiarity with the environment includes the place of residence of the driver and the number of years of residence of the driver at the place of residence, and when the position of the vehicle when it is determined that the object approaches the vehicle so that the object may collide with the vehicle is the location of residence of the driver, the processor sets the time threshold shorter the longer the number of years of residence of the driver.

Further, it is preferable that the processor sets the time threshold when the position of the vehicle when it is determined that the object approaches the vehicle so that the object may collide with the vehicle is the location of residence of the driver to be shorter than the time threshold when the position of the vehicle is not the location of residence of the driver.

In addition, in the driving support apparatus, it is preferable that the information representing the degree of familiarity with the environment includes the number of times the driver travels in each predetermined area or each predetermined road section, and the processor sets the time threshold to be shorter as the driver travels more times in the area or road segment containing the position of the vehicle when it is determined that the object approaches the vehicle so that the object may collide with the vehicle.

Furthermore, it is preferable that the processor is further configured to record the reaction time from notifying the driver of the approach of the object so that the object may collide with the vehicle until the driver performs the operation of the vehicle to avoid the collision, and learn the timing in response to the reaction time and the degree of familiarity with the environment for the driver at the position of the vehicle when it is determined that the object approaches the vehicle so that the object may collide with the vehicle.

According to another embodiment, a driving support method is provided. The driving support method includes: detecting an object existing around a vehicle based on a sensor signal representing a situation around the vehicle obtained by a sensor mounted on the vehicle; determining whether or not the object approaches the vehicle so that the object may collide with the vehicle; and notifying a driver of the approach via a notification device mounted on the vehicle at a timing corresponding to the degree of familiarity with the environment for the driver of the vehicle that is stored in a memory, when it is determined that the object approaches the vehicle so that the object may collide with the vehicle.

According to still another embodiment, a non-transitory recording medium having recorded thereon a computer program for driving support is provided. The computer program includes instructions for causing a processor mounted on a vehicle to execute a process including: detecting an object existing around the vehicle based on a sensor signal representing a situation around the vehicle obtained by a sensor mounted on the vehicle; determining whether or not the object approaches the vehicle so that the object may collide with the vehicle; and notifying a driver of the approach via a notification device mounted on the vehicle at a timing corresponding to the degree of familiarity with the environment for the driver of the vehicle that is stored in a memory, when it is determined that the object approaches the vehicle so that the object may collide with the vehicle.

The driving support apparatus according to the present invention has the effect that the approach of the object to the vehicle can be informed to the driver of the vehicle at an appropriate timing.

BRIEF DESCRIPTION OF DRAWINGS

FIG. 4 is a functional block diagram of the processor of the electronic control unit relating to the driving support processing.

FIG. 5A is a diagram illustrating an exemplary relationship between notification times for an approach of an object and the degree of familiarity with the environments of the drivers.

FIG. 5B is a diagram illustrating an exemplary relationship between notification times for an approach of an object and the degree of familiarity with the environments of the drivers.

DESCRIPTION OF EMBODIMENTS

Hereinafter, a driving support apparatus, a driving support method and a driving support computer program executed by the driving support apparatus, and a driving support system including the driving support apparatus will be described with reference to the drawings. This driving support apparatus notifies, when detecting an object approaching the vehicle, the driver of its approach. At that time, the driving support apparatus determines the timing of notifying the approach to the driver based on information representing the degree of familiarity of the driver to the environment, thereby it is possible to notify the driver of the approach of the object to the vehicle at an appropriate timing.

Figure 1:
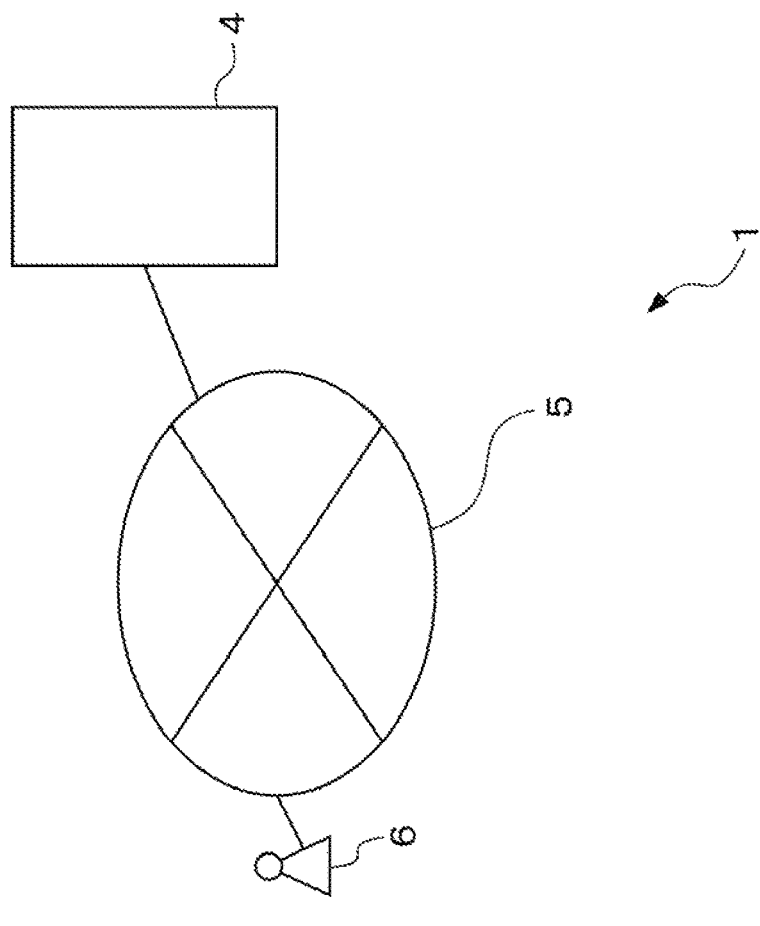
FIG. 1 is a schematic configuration diagram of a driving support system including a driving support apparatus.

FIG. 1 is a schematic configuration diagram of a driving support system including a driving support apparatus. In the present embodiment, the driving support system 1 is mounted on the vehicle 2, and includes an electronic control unit (ECU) 3 which is an example of a driving support apparatus, and a server 4. ECU3 is communicably connected to the server 4 via the radio base station 6 and the communication network 5, for example, by accessing the radio base station 6. The radio base station 6 is connected to the communication network 5 to which the server 4 is connected via a gateway (not shown) or the like. In FIG. 1, only one vehicle 2 and one ECU3 is shown, the driving support system 1 may have a plurality of vehicles 2 and the ECU3 to be mounted on each of the plurality of vehicles 2. Similarly, a plurality of radio base stations 6 may be connected to the communication network 5. The server 4 can be, for example, a server used for traffic management in a smart city or a connected city that utilizes advanced technologies such as big data.

When ECU3 detects an object (e.g., a pedestrian or other vehicle) that approaches the vehicle 2 and has a risk of colliding with the vehicle 2, it informs the driver of its approach at a timing set according to the degree of familiarity with the environment for the driver of the vehicle 2. In the present embodiment, the relationship between the degree of familiarity with the environment for the driver and the timing of notification of the approach of the object to the vehicle 2 is learned by the server 4, and updated by being notified to ECU3 of the vehicle 2. For this purpose, the server 4 acquires, from ECU3 of the vehicle 2, the response time from the notification of the approaching of the object to the vehicle 2 until the driver starts operating the vehicle 2 to avoid the collision, together with the information indicating the degree of familiarity with the environment for the driver. When the server 4 receives a set of the response time and the information representing the familiarity by a predetermined number, based on the set, learns the timing of notification of the approach of the object to the vehicle 2 according to the familiarity.

Figure 2:
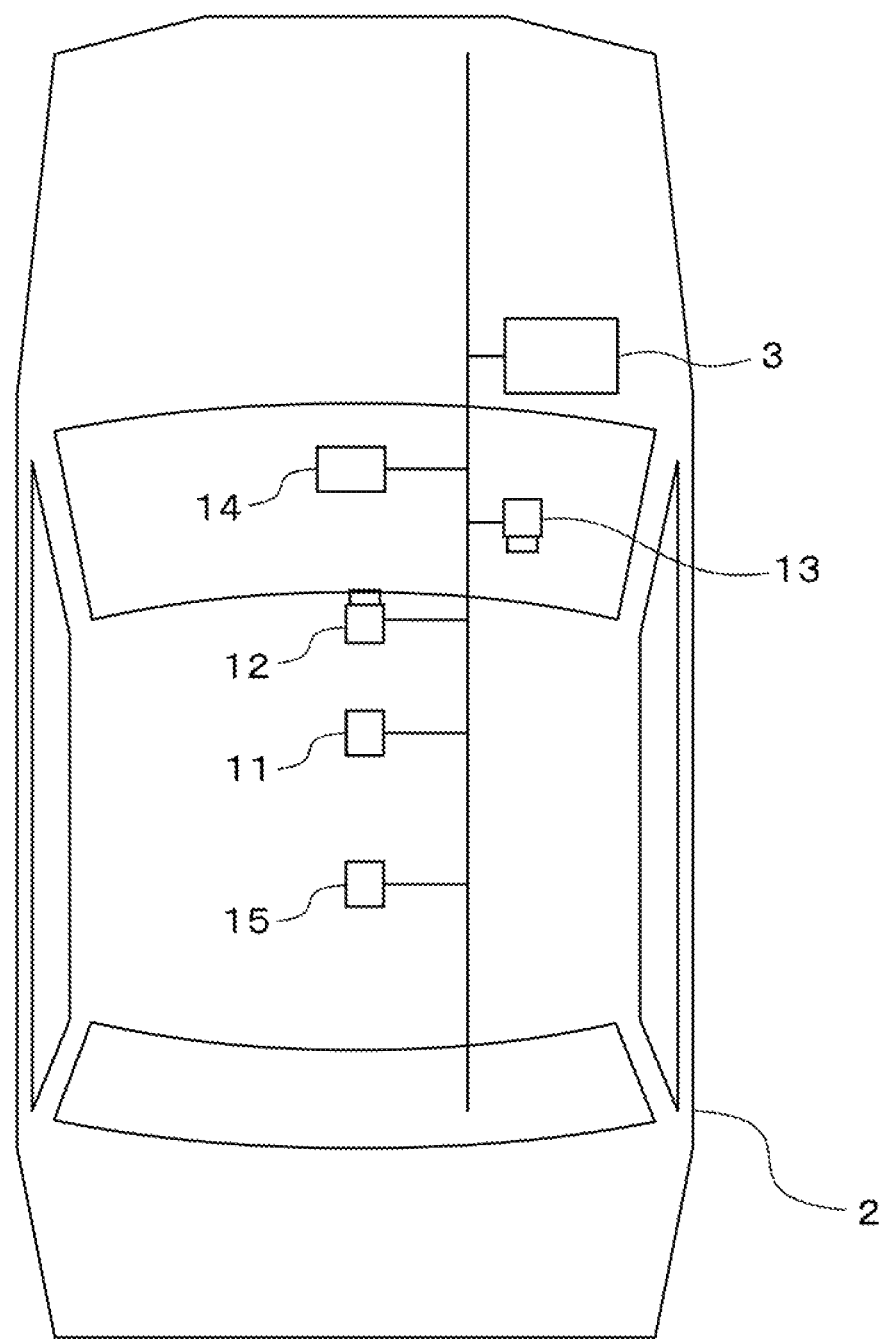
FIG. 2 is a schematic configuration diagram of a vehicle on which the driving support apparatus is mounted.

FIG. 2 is a schematic configuration diagram of a vehicle 2 on which the driving support apparatus is mounted. In the present embodiment, the vehicle 2 includes a GPS receiver 11, a camera 12 for photographing the periphery of the vehicle 2, a driver monitor camera 13 for photographing the driver of the vehicle 2, a notification device 14, a wireless communication terminal 15, and a ECU3 which is an example of a driving support apparatus. The GPS receiver 11, the camera 12, the driver monitor camera 13, the notification device 14, and the wireless communication terminal 15 are communicably connected to ECU3 via an in-vehicle network conforming to a standard such as a controller area network.

The GPS receiver 11 is an example of a position measuring unit, receives the GPS signal from the GPS satellite at every predetermined period, and measures the self-position of the vehicle 2 based on the received GPS signal. Then, the GPS receiver 11 outputs the positioning information representing the positioning result of the self-position of the vehicle 2 based on the GPS signal to ECU3 via the in-vehicle network, at every predetermined period. In addition, the vehicle 2 may have a receiver conforming to the satellite positioning system other than the GPS receiver 11. In this case, the receiver may measure self-position of the vehicle 2.

The camera 12 is an example of a sensor unit that acquires a sensor signal representing a situation around the vehicle 2. The camera 12 has a two-dimensional detector composed of an array of photoelectric conversion elements sensitive to visible light, such as a CCD or a C-MOS, and an imaging optical system for imaging an image of an area to be photographed on the two-dimensional detector. The camera 12 is attached to the vehicle 2 to capture a predetermined imaging area around the vehicle 2, for example, a front or rear area of the vehicle 2. The camera 12 photographs the predetermined imaging area at every predetermined photographing cycle (for example, 1/30 sec. to 1/10 sec.) and generates an image in which the predetermined imaging area is photographed. The generated image is an example of a sensor signal. In addition, a plurality of cameras 12 whose photographing direction or focal length are different from each other may be provided with the vehicle 2.

Each time an image is generated, the camera 12 outputs the generated image to ECU3 via an in-vehicle network.

Similar to the camera 12, the driver monitor camera 13 has a two-dimensional detector composed of an array of photoelectric conversion elements sensitive to visible light or infrared light, such as CCDs or C-MOS, and an imaging optical system for imaging an image of an area to be photographed on the two-dimensional detector. The driver monitor camera 13 may further include a light source for illuminating the driver, such as an infrared LED. The driver monitor camera 13 is then mounted to, for example, an instrument panel or vicinity thereof so that the head of the driver seated in the driver seat of the vehicle 2 is included in the imaging target area, i.e., to allow photographing of the head of the driver. The driver monitor camera 13 captures a driver at every predetermined shooting cycle (for example, 1/30 sec. to 1/10 sec.) and generates an image captured by the driver (hereinafter referred to as a driver image). The driver image obtained by the driver monitor camera 13 may be a color image or a gray image. The driver monitor camera 13 outputs the generated driver image to ECU3 via the in-vehicle network each time the driver image is generated.

The notification device 14 is provided in the cabin of the vehicle 2, and performs predetermined notification to the driver by light, voice, character display, or image display. For this purpose, the notification device 14 includes, for example, at least one of a speaker, a light source and a display device. When a notice to warn an approach of the object to the vehicle 2 is received from ECU3, the notification device 14 notifies the driver of the approach by voice from the speaker, light or flash of the light source, or the display of a warning message or warning symbol by the display device.

The wireless communication terminal 15 is an example of a communication unit and executes wireless communication processing conforming to a predetermined wireless communication standard. In the present embodiment, the wireless communication terminal 15 receives information representing the degree of familiarity with the environment for the driver and information representing the reaction time of the driver from ECU3, generates an uplink wireless signal including the information, and transmits the generated wireless signal to the wireless base station 6. In addition, the wireless communication terminal 15 receives from the radio base station 6 downlink radio signals including information indicating the relationship between the degree of familiarity with the environment for the driver and the notification timing of the approach of the object to the vehicle 2, and passes the information to ECU3.

ECU3 assists drivers in driving. In the present embodiment, ECU3 detects an object approaching the vehicle 2 based on the images obtained by the camera 12, and notifies the approach to the driver via the notification device 14.

Figure 3:
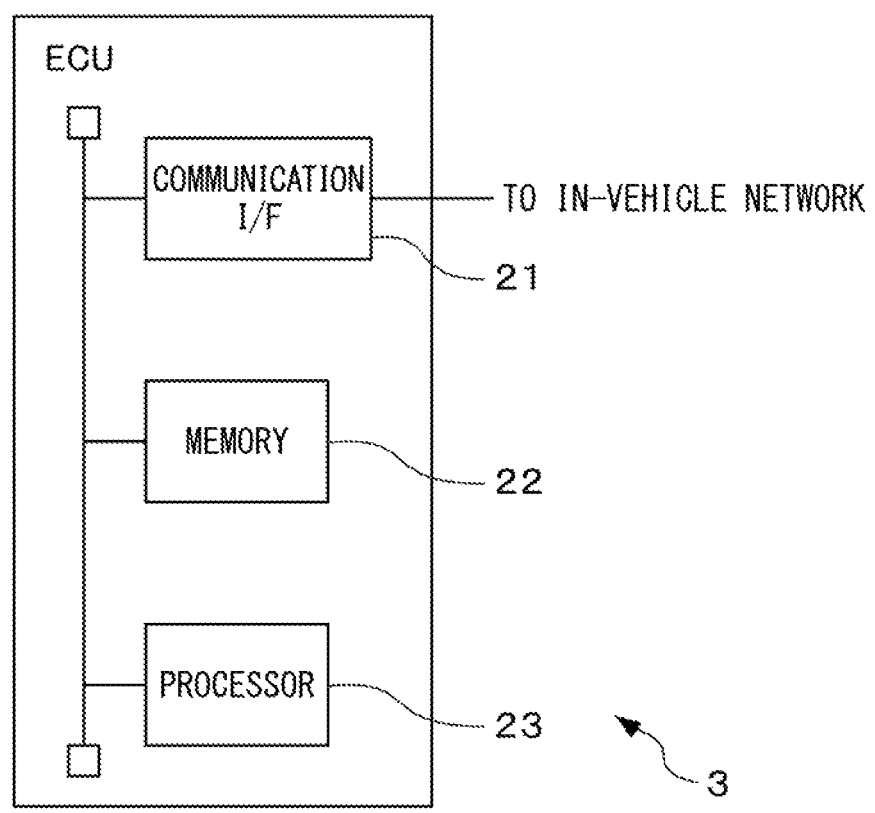
FIG. 3 is a hardware configuration diagram of an electronic control unit which is one embodiment of the driving support apparatus.

FIG. 3 is a hardware-configuration diagram of the ECU3. As shown in FIG. 3, ECU3 includes a communication interface 21, a memory 22, and a processor 23. The communication interface 21, the memory 22, and the processor 23 may each be configured as separate circuits, or may be integrally configured as one integrated circuit.

The communication interface 21 has interface circuits for connecting ECU3 to in-vehicle networks. The communication interface 21 passes the positioning information to the processor 23 each time the positioning information is received from the GPS receiver 11. Each time the communication interface 21 receives an image from the camera 12, it passes the image to the processor 23. Similarly, each time a driver image is received from the driver monitor camera 13, the communication interface 21 passes the driver image to the processor 23. In addition, when communication interface 21 receives information representing the relationship between the degree of familiarity with the environment for the driver and the timing of the notification of object proximity to vehicle 2 from the wireless communication terminal 15, it passes the information to the processor 23.

Further, when the communication interface 21 receives a notification that warns the approach of an object to the vehicle 2 from the processor 23, the communication interface 21 outputs the notification to the notification device 14. Furthermore, when the communication interface 21 receives information representing the reaction time by the driver from the notification of the approach of the object to the vehicle 2 and the degree of familiarity with the environment for the driver, the communication interface 21 outputs the information to the wireless communication terminal 15.

The memory 22 is an example of a storage unit, and includes, for example, a volatile semiconductor memory and a nonvolatile semiconductor memory. The memory 22 stores various algorithms and various data used in the driving support process executed by the processor 23 of the ECU3. For example, the memory 22 stores various parameters used for detecting an object from an image received from the camera 12 and determining whether or not the detected object approaches the vehicle 2. The memory 22 also stores identification information for identifying the driver, such as an identification number and a face image of the driver, familiarity information representing a degree of familiarity with the environment for the driver, and information representing a relationship between the degree of familiarity with the environment for the driver and a timing of notification of an approach of an object The driver identification information and the familiarity information are stored in the memory 22 for each driver registered with respect to the vehicle 2. Further, the memory 22 temporarily stores positioning information, images, driver images, and various data generated in the course of the driving support processing.

In the present embodiment, the familiarity information can be, for example, the number of years of residence in the area where the driver currently resides. This is because it is assumed that the driver will be accustomed to driving in the area with longer residence years. In this case, for example, when the driver is registered in the vehicle 2, the information representing the place of residence and the number of residence years of the driver is input via a user interface (not shown) provided in the cabin of the vehicle 2 and stored in the memory 22. The place of residence of the driver is defined as, for example, a predetermined area (for example, a circular area having a radius of several km) centered on the address where the driver resides or a predetermined administrative area (for example, any one of a city, a town, and a village) including the address. Further, the degree of familiarity information is not limited to the above example, and may be the number of travels for each predetermined area or for each predetermined section of the road. In this case, for each registered driver, a counter representing the number of travels is stored in the memory 22 for each predetermined area or for each predetermined section of the road. The processor 23 may refer to the positioning information and map information each time the vehicle 2 travels in any area or road segment to identify the traveled region or road segment and increase the value of the counter of the identified region or road segment by one for the driver while driving. Further, when the driver is registered in the vehicle 2, the driver image representing the face of the driver photographed by the driver monitor camera 13 may be stored in the memory 22 as the face image of the driver. Hereinafter, the driver registered in the vehicle 2 may be referred to as a registered driver.

In addition, the initial information representing the relationship between the degree of familiarity with the environment of the driver and the timing of notification of proximity of the object, for example, is stored in the memory 22 when the vehicle 2 is shipped. Until receiving the information representing the relationship between the degree of familiarity with the environment for the driver and the timing of notification of an approach of an object, the timing of the notification may be set according to the initial information. When ECU3 receives the information representing the relationship between the degree of familiarity with the environment for the driver and the timing of notification of an approach of an object, the initial information may be updated with the received information. Then, the timing of the notification may be set in accordance with the updated information representing the relationship between the degree of familiarity with the environment for the driver and the timing of notification of an approach of an object.

The processor 23 includes one or a plurality of CPUs (Central Processing Unit) and peripheral circuits thereof. The processor 23 may further include other arithmetic circuits, such as a logical arithmetic unit, a numerical arithmetic unit or a graphic processing unit. The processor 23 executes the driving support processing.

FIG. 4 is a functional block diagram of the processor 23 relating to the driving support processing. The processor 23 includes an identifying unit 31, a detecting unit 32, an approach judging unit 33, an informing unit 34, and a reaction time notifying unit 35. Each of these units of the processor 23 is, for example, a functional module implemented by a computer program running on the processor 23. Alternatively, each of these units included in the processor 23 may be a dedicated arithmetic circuit provided in the processor 23.

The identifying unit 31 identifies the driver based on the driver image. For this purpose, for example, the identifying unit 31 matches the driver image obtained from the driver monitor camera 13 after the ignition switch of the vehicle 2 is turned on to the face image of each registered driver stored in the memory 22. The identifying unit 31 may match the driver image to the face image of each registration driver according to any of the face authentication methods used for matching the faces represented in the image. For example, the identifying unit 31 detects each feature point of the face (e.g., the eye head, the eye tail, the nose apex, and the mouth corner point) from the driver image using template matching or an identifier, and calculates information representing the positional relationship between the detected feature points. Then, the identifying unit 31 compares the information representing the calculated positional relationship with the information representing the positional relationship between the feature points similarly detected from the face images of the respective registered drivers, thereby determining the face image most similar to the face represented in the driver image. Then, the identifying unit 31 identifies the registration driver corresponding to the face image determined to be most similar to the face represented in the driver monitor image as the driver driving the vehicle 2.

The identifying unit 31 notifies the identification number of the driver during driving to the informing unit 34. It should be noted that the driver during driving need only be identified once. Therefore, when the identification number of the driver during driving is notified to the informing unit 34, the processing of the identifying unit 31 may not be executed until the ignition switch of the vehicle 2 is turned off and then turned on again.

The detecting unit 32 detects, each time ECU3 receives an image from the camera 12, the object to be detected located around the vehicle 2 from the image. In the present embodiment, the object to be detected is an object that is at risk of colliding with the vehicle 2, for example, a moving object such as another vehicle or a pedestrian, and a structure existing on or around the road on which the vehicle 2 runs, such as a guard rail, a utility pole, or a dropped object on the road. Hereinafter, an object to be detected may be simply referred to as an object or a target object.

The detecting unit 32 detects a target object represented in an image by, for example, inputting the image to a classifier. As such a classifier, the detecting unit 32 may use a classifier based on AI or artificial intelligence technology, in particular, based on machine learning or deep learning. More specifically, the detecting unit 32 may use, as a classifier, a classifier based on a so-called neural network, for example, a deep neural network (DNN) having a convolutional neural network (CNN) type architecture such as Single Shot MultiBox Detector or Faster R-CNN. Alternatively, the detecting unit 32 may use a classifier based on another machine-learning technique, such as a AdaBoost classifier. Such a classifier is learned in advance so as to detect an object to be detected from an image by using big data such as a large number of teacher images.

The classifier outputs information representing a region in which the detected object is represented (hereinafter, referred to as an object region). For example, the classifier outputs a circumscribed rectangle surrounding the object as such information. The detecting unit 32 passes information representing the object region to the approach judging unit 33 for each of the detected objects.

According to a modification, the vehicle 2 may provide with a distance sensor (not shown) which measure the distance to the object present around the vehicle 2, for each azimuth and outputs a ranging signal representing the measurement result. In this case, the detecting unit 32 may detect an object present around the vehicle 2 based on the ranging signal from the distance sensor. Note that, the distance sensor is another example of a sensor for obtaining a sensor signal representing the surrounding situation of the vehicle, and the ranging signal is another example of the sensor signal. In this case also, the detecting unit 32 may detect an object around the vehicle 2 from a ranging signal by inputting the ranging signal to a classifier learned in advance so as to detect the object around the vehicle 2. Alternatively, the detecting unit 32 may detect an object around the vehicle 2 according to other techniques of detecting an object from the ranging signal. In this case, for each of the detected objects, the detecting unit 32 passes information indicating the orientation and distance to the object to the approach judging unit 33.

The approach judging unit 33 determines, for each of the objects detected by the detecting unit 32, whether or not approach to the vehicle 2 so that there is a risk of colliding with the vehicle 2. For this purpose, the approach judging unit 33 tracks each of the objects detected by the detecting unit 32 to predict the trajectory of the object to the predetermined time ahead. The approach judging unit 33 calculates, for each object being tracked, the distance between the object at the predicted position on the trajectory (hereinafter, sometimes referred to as the predicted position) at each future point in time and the predicted position of the vehicle 2. Then, the approach judging unit 33 determines that, when the distance for any object being tracked from the predicted position of the vehicle 2 at any time point becomes equal to or less than a predetermined threshold value, the object being tracked approaches so that there is a risk of collision with the vehicle 2. In the following, the predicted time from the current time until the distance between the predicted position of the object being tracked and the predicted position of the vehicle 2 is equal to or less than the predetermined threshold value is referred to as the collision predicted time.

In this case, the approach judging unit 33 applies a tracking process based on the optical flow, such as Lucas-Kanade method, to the object area of interest in the latest image obtained by the camera 12 and the object region in the previous image, thereby tracking the object represented in the object region. Therefore, the approach judging unit 33 extracts a plurality of feature points from the object area by applying a filter for extracting a feature point such as a SIFT or a Harris operator to the object region of interest, for example. Then, the approach judging unit 33 may calculate the optical flow by specifying, for each of the plurality of feature points, a corresponding point in the object region in the past image according to the applied tracking method. Alternatively, the approach judging unit 33 may track the object represented in the object area by applying another tracking method which is applied to the tracking of the moving object detected from the image to the object region of interest in the latest image and the object region in the past image.

The approach judging unit 33 executes the viewpoint conversion process for each object being tracked using information such as the optical axis direction, the focal length, and the installation height of the camera 12 to convert the coordinates in the image of the object into coordinates on the bird's-eye image (bird's-eye coordinates) based on the position of the camera 12. Then, the approach judging unit 33 performs a predicting process using a Kalman Filter, a Particle filter, or the like on the bird's-eye coordinates obtained from the series of images obtained during tracking, using the positions of the vehicles 2 when the series of images are obtained. Thus, the approach judging unit 33 can estimate the predicted trajectory of the object up to a predetermined time ahead. The position of the vehicle 2 at the time of each image acquisition, for example, can be the position of the vehicle 2 represented in the positioning information when the image is acquired. Alternatively, the position of the vehicle 2 at the time of each image acquisition may be estimated by comparing the image and the map information and obtaining the position of the vehicle when each feature represented in the image and the corresponding feature represented in the map information matches best.

Further, when the object is detected based on the ranging signal, the approach judging unit 33 may estimate the prediction trajectory of the object by performing the prediction process based on the orientation and distance to the object from the vehicle 2 in the individual ranging signal and the position of the vehicle 2 at the time of each ranging signal acquisition.

Furthermore, the approach determination unit 33 may calculate the predicted position of the vehicle 2 at each time point up to a predetermined time point, based on the vehicle speed, acceleration and yaw rate of the vehicle 2 in the most recent predetermined period. The ECU3 may acquire the yaw rate, vehicle speed and acceleration from the yaw rate sensor (not shown), the vehicle speed sensor (not shown) and the acceleration sensor (not shown) mounted on the vehicle 2.

According to a modification, ECU3 may control each part of the vehicle 2 so as to travel along a lane in which the vehicle 2 is located (hereinafter referred to as an ego lane). In such a case, the approach judging unit 33 may determine that, when any object being tracked is located on the ego lane and in front of the vehicle 2, the object approaches such that there is a risk of colliding with the vehicle 2. In this case, the approach judging unit 33 may calculate the collision prediction time by dividing the estimated value of the distance to the object by the current vehicle speed of the vehicle 2.

The approach judging unit 33 notifies the informing unit 34 of the determination result when it is determined that any object being tracked approaches so that there is a risk of colliding with the vehicle 2. Further, the approaching judging unit 33 notifies the predicted collision time to the informing unit 34.

When the informing unit 34 receives from the approaching judging unit 33 the judgment result that any object being tracked approaches to the vehicle 2 so that there is a risk of collision with the vehicle 2, the informing unit 34 reads from the memory 22 a time threshold indicating the timing of informing the approaching of the object to the vehicle 2 and according to the degree of familiarity with the environment for the driver. The information representing the relationship between the degree of familiarity with the environment for the driver and the time threshold is an example of the information representing the relationship between the degree of familiarity with the environment for the driver and the timing of notifying the approaching of the object. The informing unit 34 reads out information indicating the degree of familiarity with the environment for the driver in accordance with the identification information of the driver notified from the identifying unit 31.

As described above, when the information indicating the degree of familiarity with the environment for the driver is the place of residence and the number of years of residence of the driver, the informing unit 34 determines whether or not the current position of the vehicle 2 specified by the positioning information received from the GPS receiver 11 is the place of residence of the driver. When the current position of the vehicle 2 is the place of residence of the driver, the informing unit 34 reads a time threshold corresponding to the number of years of residence of the driver from the memory 22. On the other hand, when the current position of the vehicle 2 is not the place of residence of the driver, the informing unit 34 reads the time threshold corresponding to the outside of the place of residence of the driver from the memory 22. It is assumed that the longer the number of years of residence, the more the driver is accustomed to driving the vehicle 2 in the vicinity of its residence area, and the quicker the reaction to the notification of the approach of the object to the vehicle 2. Therefore, in the initial information representing the relationship between the degree of familiarity with the environment for the driver and the timing of the notification of approach of the object, the longer the number of residence years, the shorter the time threshold is set. Also, when the current position of the vehicle 2 is not the driver's residence, the driver may not be accustomed to driving the vehicle 2 near the current position of the vehicle 2. Therefore, the time threshold when the current position of the vehicle 2 is not the location of residence of the driver is set longer than the time threshold when the current position of the vehicle 2 is the location of residence of the driver.

When the information indicating the degree of familiarity with the environment for the driver is the number of travels for each predetermined area or for each predetermined road section, the informing unit 34 reads the number of travels for the area or road section including the current position of the vehicle 2 from the memory 22. Then, the informing unit 34 reads the time threshold value corresponding to the number of travels from the memory 22. In this case, the greater the number of runs for an area or road section containing the current position of the vehicle 2, the more the driver is familiar with the driving of the vehicle 2 near the current position of the vehicle 2, it is assumed that the quicker the reaction to the notification of the approach of the object to the vehicle 2. Therefore, in the initial information representing the relationship between the degree of familiarity with the environment for the driver and the timing of the notification of approach of the object, the greater the number of traveling, the time threshold is set shorter.

The informing unit 34 compares the collision prediction time with the read time threshold. When the collision prediction time is equal to or less than the time threshold, the informing unit 34 outputs a notification for warning the approach of the object to the vehicle 2 to the notification device 14 to notify the approach to the driver. On the other hand, when the collision prediction time is longer than the time threshold, the informing unit 34 does not notify the driver of the approach of the object to the vehicle 2. As a result, the informing unit 34 can suppress the driver from feeling troublesome due to the fact that the informing of the approach is too early, while ensuring a time sufficient for the driver to sufficiently respond to the approach of the object to the vehicle 2.

FIGS. 5A and 5B are diagrams showing an example of the relationship between the degree of familiarity with the environment for the driver and the notification timing of the approach of the object, respectively. In FIGS. 5A and 5B, the horizontal axis represents time. It is assumed that the length of the collision prediction time Tp shown in FIG. 5A is equal to the length of the collision prediction time Tp shown in FIG. 5B.

FIG. 5A illustrates a case where the driver is accustomed to the environment. In this example, since the driver is accustomed to the environment, the time threshold Thm is set relatively short, so that the collision prediction time Tp is longer than the time threshold Thm. Therefore, the approaching of the object is not notified at the current time t. When the predicted collision time Tp becomes shorter than or equal to the time threshold Thm due to the behavior of the object after the current time, the approaching of the object is notified to the driver at that time. On the other hand, when the collision between the object and the vehicle 2 is not predicted due to the behavior of the object after the current time, as a result, the approaching of the object is not notified to the driver, and therefore the driver does not need to be informed unnecessarily.

FIG. 5B illustrates a case where the driver is not accustomed to the environment. In this example, since the driver is not accustomed to the environment, the time threshold Thm is set relatively long, so that the collision prediction time Tp is shorter than the time threshold Thm. Therefore, at the current time t, the approaching of the object is notified to the driver. In this example, even if the collision prediction time Tp is relatively long, the approaching of the object is notified to the driver, and therefore, even if the driver is not accustomed to the environment, the time for the driver to cope with the approaching of the object is sufficiently secured.

The reaction time notifying unit 35 measures a reaction time from the notification of the approach of the object to the vehicle 2 until the driver performs an operation for avoiding the collision with the object, which may be simply referred to as a reaction time hereinafter. The operation for avoiding the collision is, for example, the operation of the brake for decelerating the vehicle 2, or the operation of the steering for changing the course of the vehicle 2. The reaction time notifying unit 35 transmits to the server 4 via the wireless communication terminal 15 the reaction time and information indicating the degree of familiarity with the environment for the driver at the position of the vehicle 2 when the approaching of the object to the vehicle 2 is notified.

Figure 6:
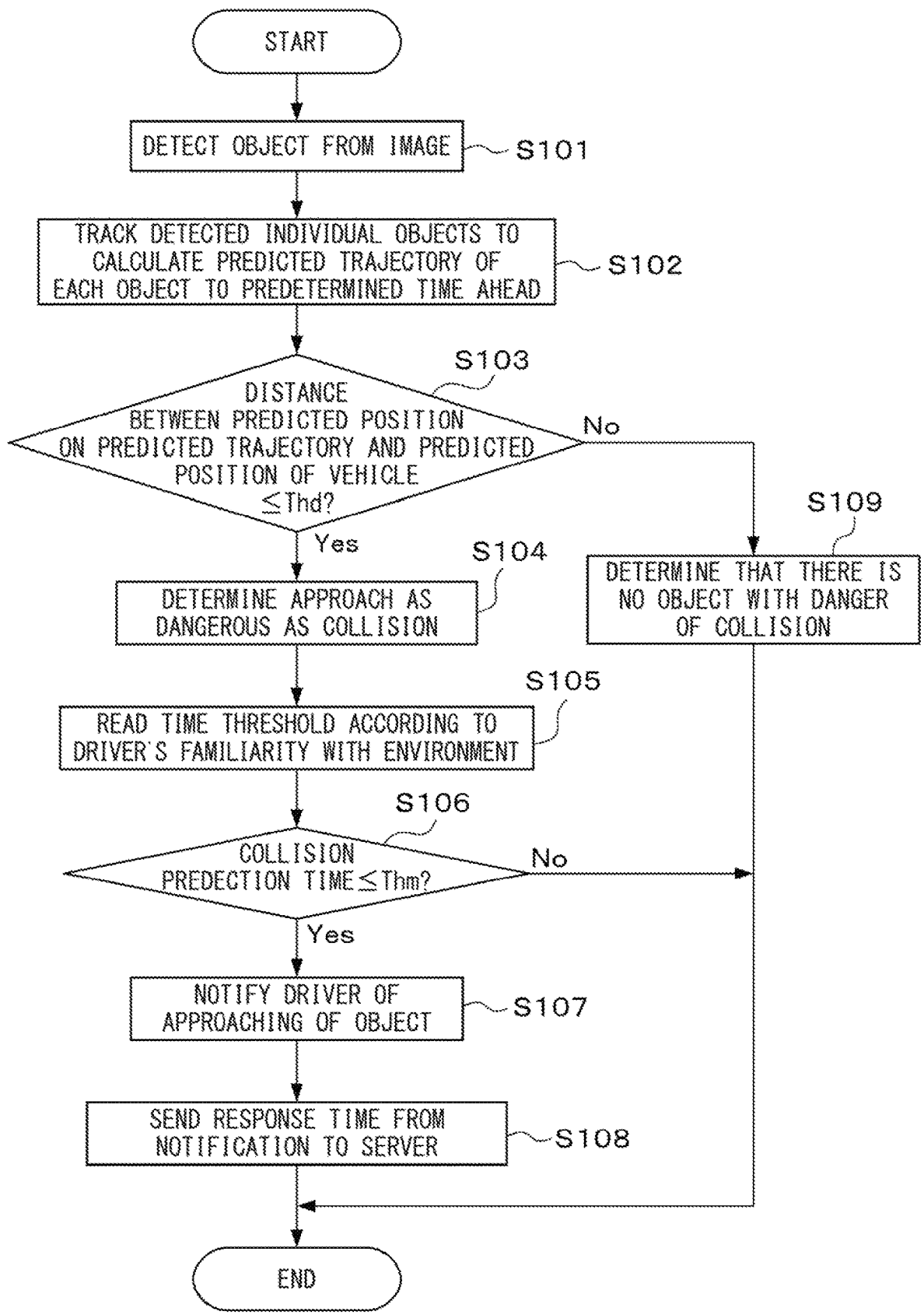
FIG. 6 is an operation flowchart of the driving support process according to the electronic control unit.

FIG. 6 is an operation flow chart of the driving support process in the ECU3. Each time the processor 23 of the ECU 3 receives an image from the camera 12, the processor 23 performs the driving support process according to the following operational flow chart.

Each time the ECU3 receives an image from the camera 12, the detecting unit 32 of the processor 23 detects an object to be detected, which is located around the vehicle 2, from the image (step S101).

The approach judging unit 33 of the processor 23 tracks each of the objects detected by the detecting unit 32, thereby obtaining a predicted trajectory of the object up to a predetermined time-ahead (step S102). Then, the approach judging unit 33 determines whether or not the distance between each predicted position on the predicted trajectory up to the predetermined time ahead and the predicted position of the vehicle 2 is equal to or less than the predetermined threshold Thd for each of the objects being tracked (step S103). For any object, when the distance between the predicted position on the predicted trajectory at any time point and the predicted position of the vehicle 2 is equal to or less than the threshold Thd (step S103—Yes), the approach judging unit 33 determines that the object approaches to the vehicle 2 so that there is a risk of colliding with the vehicle 2 (step S104).

The informing unit 34 of the processor 23 reads the time threshold Thm corresponding to the degree of familiarity with the environment for the driver from the memory 22 (step S105). Then, the informing unit 34 determined, for the object which is determined to approach to the vehicle 2 so that the object may collide with the vehicle 2, the collision predicting time until the predicted distance between the predicted position of the object and the predicted position of the vehicle 2 is equal to or less than the predetermined threshold Thd (step S106). When the collision predicted time is equal to or less than the time threshold Thm (step S106—Yes), the informing unit 34, to the drivers, notifying the approach of the object to the vehicle 2 via the notification device 14 (step S107). Thereafter, the reaction time notifying unit 35 of the processor 23 measures the reaction time from the notification of the approach of the object to the vehicle 2 until the driver performs the operation for avoiding the collision with the object. Then, the reaction time notifying unit 35 transmits information representing the response time and the degree of familiarity with the environment for the driver to the server 4 via the radio communication terminal 15 (step S108). Then, the processor 23 ends the driving support process.

On the other hand, when the distance between the predicted position on the predicted trajectory and the predicted position of the vehicle 2 for any of the objects being tracked does not become equal to or less than the predetermined threshold value Thd (step S103-No), the approach judging unit 33 determines that there is no object so close that there is a risk of colliding with the vehicle 2 (step S109). Then, the processor 23 ends the driving support process. In addition, in step S106, when the predicted collision time is longer than the time threshold Thm (step S106-No), the processor 23 terminates the driving support process without notifying the driver of the approach of the object.

Figure 7:
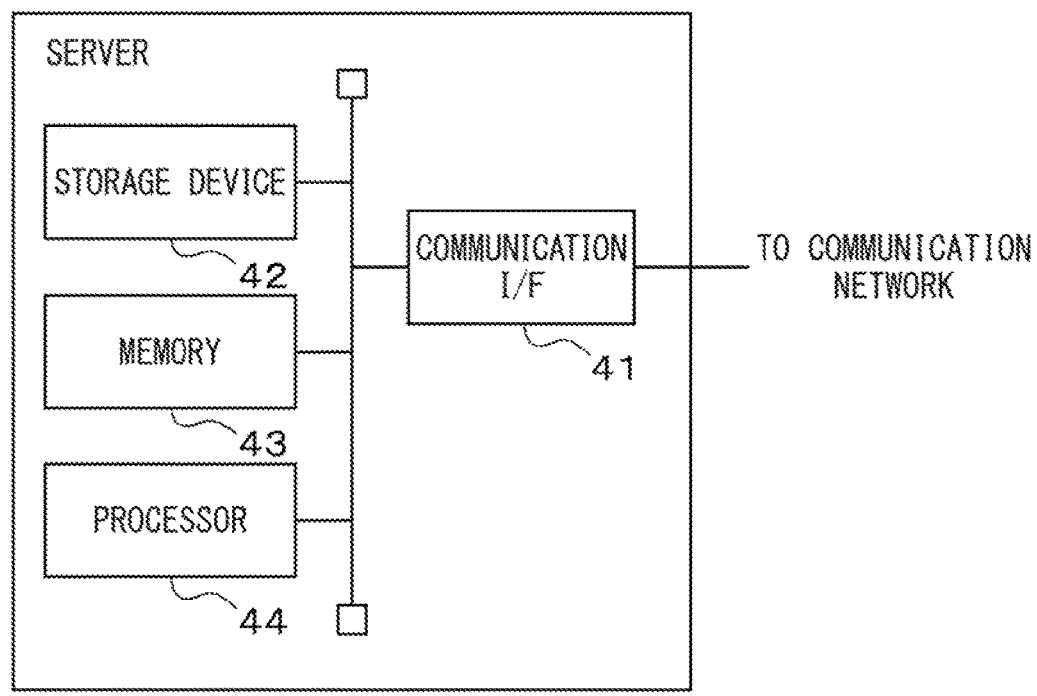
FIG. 7 is a hardware configuration diagram of a server.

Next, the server 4 will be described. FIG. 7 is a hardware configuration diagram of the server 4. The server 4 includes a communication interface 41, a storage device 42, a memory 43, and a processor 44. The communication interface 41, the storage device 42, and the memory 43 are connected to the processor 44 via signal lines. The server 4 may further include an input device such as a keyboard and a mouse, and a display device such as a liquid crystal display.

The communication interface 41 is an example of a communication unit, and includes an interface circuit for connecting the server 4 to the communication network 5. The communication interface 41 is configured to be able to communicate with the vehicle 2 via the communication network 5 and the radio base station 6. That is, the communication interface 41 passes information indicating the reaction time of the driver and the degree of familiarity with the environment for the driver received from the vehicle 2 via the radio base station 6 and the communication network 5 to the processor 44. In addition, the communication interface 41 transmits, to the vehicle 2 via the communication network 5 and the radio base station 6, information indicating the relationship between the degree of familiarity with the environment for the driver and the timing of notification of the approach of the object to the vehicle 2, which is received from the processor 44.

The storage device 42 is an example of a storing unit, and includes, for example, a hard disk device, an optical recording medium, and an access device thereof. The storage device 42 stores information indicating the reaction time of the driver and the degree of familiarity with the environment for the driver. The storage device 42 may further store identification information of the vehicle 2. In addition, the storage device 42 may store a computer program executed on the processor 44 to perform a learning process to learn the relationship between the degree of familiarity with the environment for the driver and the timing of notification of approach of the object to the vehicle 2. Furthermore, the storage device 42 may store information representing the relationship between the degree of familiarity with the environment for the driver and the timing of notification of the approach of an object to the vehicle 2.

The memory 43 is another example of the storing unit, and includes, for example, a nonvolatile semiconductor memory and a volatile semiconductor memory. The memory 43 temporarily stores various data generated during the execution of the learning process, various data acquired by communication with the vehicle 2, and the like.

The processor 44 is an example of a control unit and includes one or a plurality of CPUs (Central Processing Unit) and peripheral circuits thereof. The processor 44 may further include other arithmetic circuits, such as a logical arithmetic unit or a numerical arithmetic unit. The processor 44 executes the learning process when a predetermined number or more of pieces of information representing the reaction time of the driver and the degree of familiarity with the environment for the driver are accumulated.

Figure 8:
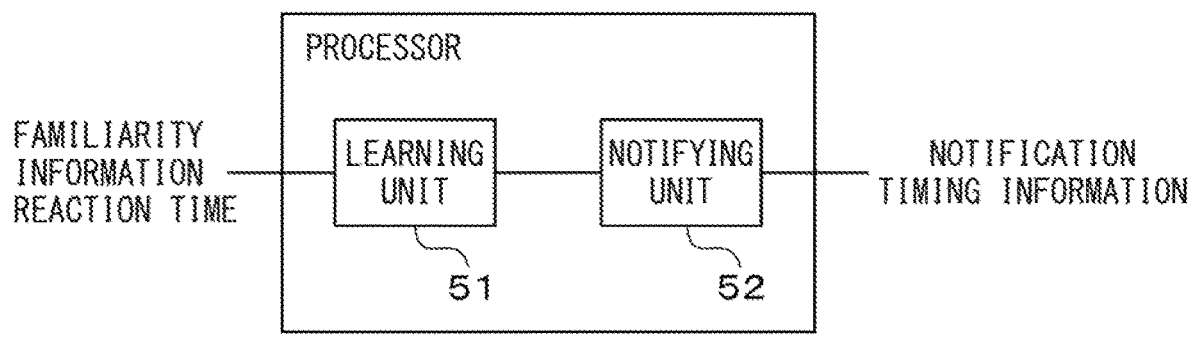
FIG. 8 is a functional block diagram of a server's processor with respect to learning processing.

FIG. 8 is a functional block diagram of the processor 44 relating to the learning process. The processor 44 includes a learning unit 51 and a notifying unit 52. Each of these units of the processor 44 is a functional module implemented by a computer program executed on the processor 44. Alternatively, each of these units included in the processor 44 may be a dedicated arithmetic circuit provided in the processor 44.

The learning unit 51 calculates the timing of notifying the approaching of the object to the vehicle 2 according to the degree of familiarity with the environment for the driver based on the degree and the reaction time. For example, the learning unit 51 calculates an average value of the reaction time for each degree of familiarity with the environment for the driver, for example, for each residence year or for each number of times of travel. The learning unit 51 sets, for each degree of familiarity with the environment for the driver, a value obtained by adding a predetermined offset time to the average value of the response time with respect to the degree of familiarity as the timing (the time threshold described above) of notification of the approach of the object to the vehicle 2 with respect to the degree of familiarity. As a result, the learning unit 51 can set an appropriate notification timing according to the degree of familiarity with the environment for the driver.

Alternatively, the learning unit 51 uses the combination of the degree of familiarity with the environment for the individual drivers and the response time as individual data included in the big data to learn a learning model for calculating the timing of notifying the approach of the object to the vehicle 2 according to the degree of familiarity with the environment for the driver. Such a learning model may be based on AI or artificial intelligence. More specifically, such a learning model may be based on machine learning or deep learning, such as a neural network. The learning unit 51 may use such a learning model to calculate the timing of notification for each degree of familiarity with the environment for the driver.

The notifying unit 52 generates notification timing information including the timing of notification of the proximity of the object to the vehicle 2 for each degree of familiarity with the environment for the driver when the timing of notification for each degree of familiarity with the environment for the driver is calculated by the learning unit 51. The notifying unit 52 notifies the vehicle 2 of the generated notification timing information via the communication interface 41, the communication network 5, and the radio base station 6.

As described above, since the driving support apparatus determines the timing of notifying the approach of the object to the vehicle to the driver based on the information representing the degree of familiarity with the environment for the driver, the driving support apparatus can notify the driver of the approach of the object to the vehicle at an appropriate timing.

According to a modification, the timing of the notification of the approach of an object to the vehicle 2 may be determined based not only on the degree of familiarity with the environment for the driver, but also on driving proficiency of the driver with the vehicle 2, or on the environment itself around the vehicle 2. For example, it is assumed that the lower the driving proficiency of the driver with the vehicle 2 is, the longer the driver's reaction time from the notification of the approaching of the object to the vehicle 2 becomes. Further, as the environment around the vehicle 2 is an environment that makes it difficult for the driver to drive the vehicle 2, it is preferable that the approach of the object to the vehicle 2 is informed to the driver as soon as possible. Therefore, the notifying unit 34 may correct the timing of the notification determined according to the degree of familiarity with the environment for the driver so that the notification is made earlier, as the driving proficiency of the vehicle 2 of the driver is lower or as the environment around the vehicle 2 is more difficult for driving.

For example, the notifying unit 34 may correct the time threshold so that the time threshold is longer, as the driving proficiency of the vehicle 2 of the driver is lower, or as the environment around the vehicle 2 is more difficult for driving. The driver's driving proficiency with respect to the vehicle 2 can be represented by, for example, the number of years since the driver purchased the vehicle 2, or the number of years since the driver acquired the driver's license. In this case, the shorter these years is, the lower the driving proficiency of the driver about the vehicle 2 is. Like the information indicating the place of residence and the number of years of residence of the driver, for example, when the driver is registered in the vehicle 2, these years may be input through a user interface (not shown) provided in the cabin of the vehicle 2 and stored in the memory 22. In addition, with respect to the environment around the vehicle 2, it is supposed that, for example, it is more difficult for driving at night, rainy weather, narrower roads or points where convergence is present than daytime, clear weather, wider roads or points where there is no convergence. Therefore, the notifying unit 34 may correct the timing of the notification determined according to the degree of familiarity with the environment for the driver so that the timing is earlier, when the current time obtained from the clock provided in the vehicle 2 (not shown) is included in the time zone corresponding to the night. Alternatively, the notifying unit 34 may correct the timing of the notification determined according to the degree of familiarity with the environment for the driver so that the more rainfall is detected by the rainfall sensor provided in the vehicle 2 (not shown), the earlier the timing is. Alternatively, the notifying unit 34 determines whether the current position of the vehicle 2 is a merging point or the width of the road at the current position of the vehicle 2 is equal to or less than a predetermined width, with reference to the current position of the vehicle 2 represented in the positioning information and the map information. When the current position of the vehicle 2 is a merging point, or the width of the road at the current position of the vehicle 2 is equal to or less than the predetermined width, the notifying unit 34 corrects the timing of the notification determined according to the degree of familiarity with the environment for the driver, so that the timing is earlier. In this manner, the notifying unit 34 can notify the driver of the approach at a more appropriate timing by correcting the timing of notifying the approach of the object in accordance with the driver's driving familiarity with the vehicle 2 or the environment surrounding the vehicle 2.

Further, the learning unit 51 of the processor 44 of the server 4 may learn the timing of the notification for each combination of the degree of familiarity with the environment for the driver, the driving proficiency of the driver and the environment around the vehicle 2 in accordance with the reaction time for each combination, similarly to the above embodiment. In this case, the reaction time notifying unit 35 of the processor 23 of ECU3 may transmit the information indicating the reaction time and the degree of familiarity, as well as the information indicating the driving proficiency of the driver and the environment around the vehicles 2, to the server 4.

According to another modification, processor 23 of ECU 3 may perform the same learning process as the learning unit 51 of the processor 44 of the server 4. In this case, the reaction time notifying unit 35 may store information indicating the reaction time and the degree of familiarity with the environment for the driver in the memory 22 so that the learning unit 51 provided in the processor 23 can use the information. The server 4 may be omitted. Further, when the driver of the vehicle 2 is limited to a specific person in advance, the process of the identification unit 31 may be omitted.

ECU3 according to the above-described embodiment or modifications may be implemented in vehicles to which not only manual operation control but also automatic operation control is applicable. The computer program for realizing the functions of the processor 23 of ECU3 according to the above-described embodiment or modifications may be provided in a form recorded on a computer-readable portable recording medium such as a semi-conductor memory, a magnetic recording medium, or an optical recording medium.

As described above, those skilled in the art can make various changes within the scope of the present invention in accordance with the embodiments to be implemented.

What is claimed is:

1. A driving support apparatus comprising:
    a memory configured to store information representing a degree of familiarity with an environment for a driver of a vehicle; and
    a processor configured to detect an object existing around the vehicle based on a sensor signal representing a situation around the vehicle obtained by a sensor mounted on the vehicle,
    determine whether or not the object approaches the vehicle such that the object may collide with the vehicle, and
    upon the processor determines that the object approaches the vehicle such that the object may collide with the vehicle, notify the driver of the approach via a notification device mounted on the vehicle at a timing corresponding to the degree of familiarity with the environment for the driver of the vehicle,
    upon the processor determines that the object approaches the vehicle such that the object may collide with the vehicle, the processor is programmed to calculate a predicted time until the collision,
    upon the processor determines that the predicted time is less than or equal to a time threshold representing the timing set to be shorter as the degree of familiarity with the environment of the driver is higher, the processor notifies the driver of the approach, and
    wherein the information representing the degree of familiarity with the environment includes a place of residence of the driver and a number of years of residence of the driver at the place of residence, and upon the processor determines that a position of the vehicle is the place of residence of the driver in correspondence with determining that the object approaches the vehicle such that the object may collide with the vehicle, the processor sets the time threshold shorter as the number of years of residence of the driver increases.

2. The driving support apparatus according to claim 1, wherein if the processor determines the position of the vehicle is at the location of residence of the driver in conjunction with the processor determining that the object approaches the vehicle such that the object may collide with the vehicle, the processor sets the time threshold to be shorter than the time threshold when the position of the vehicle is not the location of residence of the driver.

3. The driving support apparatus according to claim 1, wherein the processor is further configured to record a reaction time from notifying the driver of the approach of the object such that the object may collide with the vehicle until the driver operates the vehicle to avoid the collision, and
    learn the timing in response to the reaction time and the degree of familiarity with the environment for the driver at the position of the vehicle when the processor determines that the object approaches the vehicle such that the object may collide with the vehicle.

4. A driving support method comprising:
- storing information representing a degree of familiarity with an environment for a driver of a vehicle;
- detecting an object existing around the vehicle based on a sensor signal representing a situation around the vehicle obtained by a sensor mounted on the vehicle;
- determining whether or not the object approaches the vehicle such that the object may collide with the vehicle; and
- notifying a driver of the approach via a notification device mounted on the vehicle at a timing corresponding to the degree of familiarity with the environment for the driver of the vehicle that is stored in a memory, when it is determined that the object approaches the vehicle such that the object may collide with the vehicle,
- upon determining that the object approaches the vehicle such that the object may collide with the vehicle, calculate a predicted time until the collision,
  - upon determining that the predicted time is less than or equal to a time threshold representing the timing set to be shorter as the degree of familiarity with the environment of the driver is higher, the notify the driver of the approach, and
- wherein the information representing the degree of familiarity with the environment includes a place of residence of the driver and a number of years of residence of the driver at the place of residence, and upon determining that a position of the vehicle is the place of residence of the driver in correspondence with determining that the object approaches the vehicle such that the object may collide with the vehicle, set the time threshold shorter as the number of years of residence of the driver increases.

5. A non-transitory recording medium having recorded thereon a computer program for driving support, the program causing a processor mounted on a vehicle to execute a process comprising:
- storing information representing a degree of familiarity with an environment for a driver of a vehicle;
- detecting an object existing around the vehicle based on a sensor signal representing a situation around the vehicle obtained by a sensor mounted on the vehicle;
- determining whether or not the object approaches the vehicle such that the object may collide with the vehicle; and
- notifying a driver of the approach via a notification device mounted on the vehicle at a timing corresponding to the degree of familiarity with the environment for the driver of the vehicle that is stored in a memory, when the processor determines that the object approaches the vehicle such that the object may collide with the vehicle,
- upon the processor determines that the object approaches the vehicle such that the object may collide with the vehicle, the processor is programmed to calculate a predicted time until the collision,
- upon the processor determines that the predicted time is less than or equal to a time threshold representing the timing set to be shorter as the degree of familiarity with the environment of the driver is higher, the processor notifies the driver of the approach, and
- wherein the information representing the degree of familiarity with the environment includes a place of residence of the driver and a number of years of residence of the driver at the place of residence, and upon the processor determines that a position of the vehicle is the place of residence of the driver in correspondence with determining that the object approaches the vehicle such that the object may collide with the vehicle, the processor sets the time threshold shorter as the number of years of residence of the driver increases.

6. A driving support apparatus comprising:
- a memory configured to store information representing a degree of familiarity with an environment for a driver of a vehicle; and
- a processor configured to:
  - detect an object existing around the vehicle based on a sensor signal representing a situation around the vehicle obtained by a sensor mounted on the vehicle,
  - determine whether or not the object approaches the vehicle such that the object may collide with the vehicle,
  - upon the processor determining that the object approaches the vehicle such that the object may collide with the vehicle, notify the driver of the approach via a notification device mounted on the vehicle at a timing corresponding to the degree of familiarity with the environment for the driver of the vehicle,
  - upon the processor determining that the object approaches the vehicle such that the object may collide with the vehicle, the processor is programmed to calculate a predicted time until the collision, and
  - upon the processor determining that the predicted time is less than or equal to a time threshold representing the timing set to be shorter as the degree of familiarity with the environment of the driver is higher, the processor notifies the driver of the approach,
  - wherein the information representing the degree of familiarity with the environment includes a number of times the driver travels in each predetermined area or each predetermined road section, and the processor sets the time threshold to be shorter as the driver travels more times in the area or road segment containing the position of the vehicle when the processor determines that the object approaches the vehicle such that the object may collide with the vehicle.

* * * * *